United States Patent [19]

Weshahy

[11] Patent Number: 4,802,475
[45] Date of Patent: Feb. 7, 1989

[54] METHODS AND APPARATUS OF APPLYING INTRA-LESIONAL CRYOTHERAPY

[76] Inventor: Ahmed H. A. G. Weshahy, 11 Harrun St., Dokki, Cairo, Egypt

[21] Appl. No.: 64,619

[22] Filed: Jun. 22, 1987

[51] Int. Cl.$^4$ ............................................. A61B 17/36
[52] U.S. Cl. ......................... 128/303.1; 128/DIG. 27
[58] Field of Search ............ 128/303.1, 329 A, 329 R, 128/339, 399–403, DIG. 27, 754; 604/51, 112, 113, 115, 264, 272, 304, 308, 310

[56] References Cited

U.S. PATENT DOCUMENTS

| | | | |
|---|---|---|---|
| 3,434,477 | 3/1969 | Thomas | 128/303.1 |
| 3,608,539 | 9/1971 | Miller | 128/754 |
| 3,712,306 | 1/1973 | Bryne | 128/303.1 |
| 3,889,618 | 6/1975 | Waller et al. | 128/303.1 |
| 4,275,734 | 6/1981 | Mitchiner | 128/303.1 |
| 4,306,568 | 12/1981 | Torre | 128/303.1 |

FOREIGN PATENT DOCUMENTS

| | | | |
|---|---|---|---|
| 0216856 | 1/1985 | Fed. Rep. of Germany | 128/DIG. 27 |
| 0906553 | 2/1982 | U.S.S.R. | 128/303.1 |
| 1168224 | 7/1985 | U.S.S.R. | 604/272 |

Primary Examiner—Max Hindenburg
Attorney, Agent, or Firm—Arthur L. Plevy

[57] ABSTRACT

There is described a method of performing intra-lesional cryosurgery utilizing a specifically shaped tubular needle having a front piercing surface coextensive with an opening. The needle is introduced into the skin from one point and runs through deeper tissues based on the surface orientation of the needle. The piercing surface of the needle is directed through a second point where it emerges from the skin. The needle as indicated is a hollow tubular member and has one end which is adapted to receive a source of a cryrogen gas. The gas is passed through the needle and produces a lowering of the needle temperature. This low temperature is directed to the surrounding tissues to form an ice cylinder about the imbedded part of the needle in the deeper tissues. This ice cylinder affords to selectively freeze the tissue and thereby destroys the lesion being treated. A plurality of different shaped needles are shown to accommodate different types and different depth lesions. Some needles are also selectively insulated at various portions to cause the uninsulated portion of the needle to selectively apply freezing temperatures to tissues in selective directions.

21 Claims, 10 Drawing Sheets

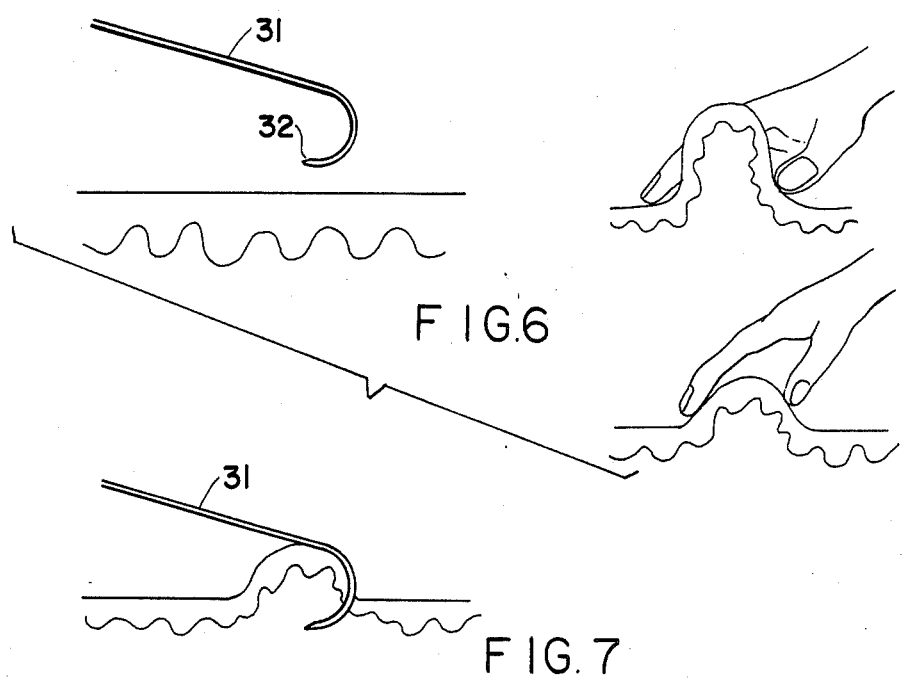
FIG.6
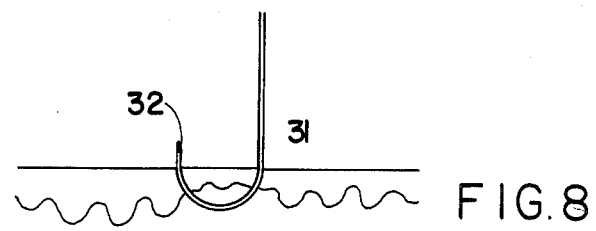
FIG.7
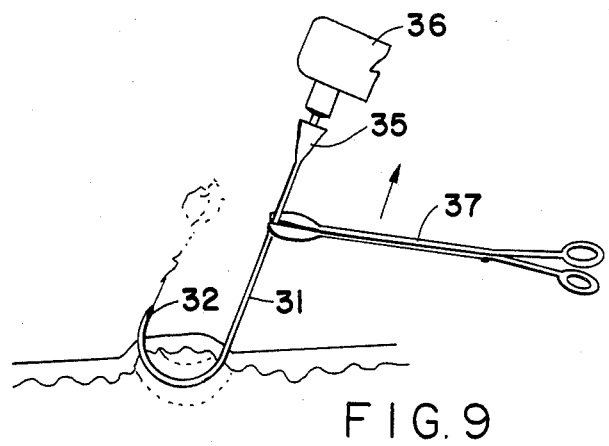
FIG.8
FIG.9

METHODS AND APPARATUS OF APPLYING INTRA-LESIONAL CRYOTHERAPY

BACKGROUND OF THE INVENTION

This invention relates to a method and apparatus for applying cryotherapy and more particularly to apparatus and methods employing specifically shaped elongated tubular needles inserted through the skin of a patient to destroy lesions by passing a cryogen through the needle.

Cryogenics are primarily concerned with the development of freezing temperatures within a biological system. Thus use of cryogenics in medicine dates back to the ancient Egyptians of 2500 BC as they found that the application of cold soothes sites of trauma and reduces inflammation.

See a text entitled "*Cryosurgery-For Skin Cancer and Cutaneous Disorders*" edited by Setrag A. Zacarian, published by The C. V. Mosby Company (1985), St. Louis, Toronto, Princeton.

The destruction of tissue by local application of refrigerants is an established surgical technique. When controlled, it will provide precise injury and at the same time spare neighboring vital structures.

Cryosurgery is based on withdrawal of heat from a biological system which will lead to freezing of the tissues and transformation of the water from solution into biologically inert ice crystals. In turn this will lead to cessation of circulation in the tissues with intra- and extra-cellular biochemical, anatomical and physiological sequel which will end in tissue anoxemia and ischemic necrosis.

The critical temperature at which cells die when they are frozen may occur between $-2°$ C. and $-4°$ C. It was found that $-50°$ C. is the optimal temperature for achieving effective cryonecrosis of malignant tumors of the skin.

The two most commonly used refrigerants in cryosurgery are nitrous oxide ($N_2O$) and liquid nitrogen ($LN_2$). The latter is the only coolant effective for malignant tumors as it has a lower boiling point up to $-195.6°$ C.

Cryosurgery is used for treating benign, premalignant and some cutaneous malignant lesions. In addition, it was found to be useful for palliative therapy of malignant conditions.

Two main techniques for cryosurgery application are reported in the literature. A spray technique (ST) in which cryogen is applied directly onto the target site and a cryoprobe technique (CP) in which the surface of the previously cooled probe (by the cryogen) is applied to the target site instead of the actual cryogen. See a text entitled "*Skin Surgery*" edited by E. Epstein, 5th Edition, Charles C. Thomas, publisher, Springfield, Ill.

The shape of the cryolesion (produced by application of either technique to the surface) is hemispherical as the ice front advances from the surface downward. This hemispherical ice ball cannot be perceived during the freezing procedure but it can be balloted by palpitation, which is adequate for the most superficial lesions, but it is of little value for the common nodular carcinomas of the skin which need measuring of the temperature in depth through thermocouple needles or other apparatus. The rate of extension of freezing slows as conditions at the periphery approach equilibrium between heat loss and heat supply by circulation. In general, the depth of freezing may be judged by the lateral spread of frost from the probe and this is used as a guide in treatment. It is just about the radius of the surface area and about half the radius of the ice ball in the cryo-spray technique.

The choice of technique is based in part on technical consideration but also in part on personal preference. The advantage of a probe technique is that it produces a more predictable area freezing, deeper penetration in addition to the possibility of pressure on the probe which increases the depth of penetration through compression of the tissue. Cryo-probes may be either applied to the surface of a lesion or inserted into the tissues (especially pointed probes) to produce deep freezing. Surface freezing with application of slight pressure is used more commonly than probe insertion as it has the advantages that no wound is caused, little or no bleeding occurs, need for anesthesia is lessened and the danger of dissemination of tumor cells are minimized. On the other hand, insertion of the probe into the tissue has its advantage in that it increases efficiency of freezing because of greater contact with the freezing surface.

Presently available probes are employed by application of the probes to the surface of the skin to transmit the cold to deeper tissues. Due to the length of time required, this technique results in damage to the overlying tissue. Such probes are available from many concerns such as the Brymill Corporation of Vernon, Conn. 06066. To achieve cooling of the probe, the gas circulates inside its lumen. The probes contain an inlet conduit and an outlet conduit both of which are associated with a probe tip. Hence, larger probes which can perform deeper penetration are wide and have diameters in excess of 3 mm. Hence, these probes are employed together with surgical procedures using scalpels, punch biopsy, electrocautery and so on. The use of the larger probes is limited due to the attendant surgical procedures requiring a large bleeding field and local anesthesia to enable the probe to be inserted at the proper depth.

There are thin probes which are about 1 mm in diameter and which are cooled by conduction. These probes are extremely short (less than 5 mm) and also require a surgical opening to reach the outer layers of the deeper tissues to be frozen.

The advantage of the spray technique is that the cryogenic agent is used at its coldest possible temperature and the spray can be moved freely about the lesion so that freezing can be extensive and wide rather than deep (as it does not compress tissues). The principal problem with the spray is that freezing is difficult to achieve and prolonged use in one area results in healthy tissue destruction. This is in addition to the possibility of gas insufflation of subcutaneous tissues and the possibility of infection with organisms which the gas may contain (as *Staphylococcus albus*).

The destruction of a deeper tissue by the commonly used techniques need more destruction of the superficial tissues as the cooling starts from above. This will lead usually to unwanted manifestations and uncommonly to some complications. The undesirable clinical manifestations start by wheal formation due to liberation of histamine from degranulated mast cells. This is usually followed by formation of a bulla due to dermal-epidermal separation while with deeper freezing the blister does not develop. The bulla may be hemorrhagic and sersanguineous exudate may persist coming out up to 10 days or more. Oedema and crust formation usually follow and complete re-epithelization may not take place (in some lesions) before two months of cryosurgery. In addition to the hypertropic scars and pigmentary disorders, other less common complications were reported as: pain, post-operative infection, debilitating oedema, development of pyogenic granuloma, and nerve damage. Also the possibility of nitrogen hypoxia exists when working near the nostrils or mouth. Although success in curing some lesions by cryosurgery (as Actinic Keratosis) may reach up to 98%, the problems of recurrence and incomplete cure differ among the lesions with different pathologic natures.

As a result, many authors did not find the ordinary methods and instrumentations of cryosurgery satisfactory in regard to ease of application, efficacy and optimum cosmetic results. This was especially true of lesions with different groups of patients especially poor risk patients because of the associated diseases and advanced age. So some investigators had been forced to modify the known techniques (ST, CP).

Some of the modifications concerned the instrumentation, as using different probes and using clear plastic cones to allow control of the lateral spray and visualization of the frost during freezing. Other modifications were concerned with the methods of application as debulking of the keratotic lesions, combination of electrocautery or partial excision or curretage with cryotherapy and application of both spray and probe techniques through the biopsy site.

In spite of the available modifications, the problem of producing and determining of effective freezing in depth seems to be still unsolved, a hope which attracted the effort of some investigators.

Some authors tried to use other aids to determine the depth of the ice front. Zacarian D., made an experiment using ultrasound and hoped for a visual demonstration of the evolving cryolesion. But, during the freezing state, the ultrasound was unable to detect the hemispherical ice formation or depth of the ice front below the skin surface and within the tumor. He stated that further devices should include the ability to visualize and measure the volume of the evolving cryolesion and detect the advancing hemispherical ice front during cryosurgery.

Gage A. stated that the chief limitation with cryosurgery is the difficulty in freezing sufficient tissue (especially for large cancers). The best of presently available apparatus is barely adequate because tissues are poor conductors of heat that limits extension of freezing. The amount of tissue that can be frozen in a single application of a probe is small in comparison with many lesions. Depth of freezing beyond 2 cm. is difficult to achieve. Multiple applications of the probe, insertion of the probe into bulky lesions and repetition of freezing at a later date are the methods of compensating for the difficulty of freezing sufficient tissue. Still these do not ensure capability of freezing large cancers. Inevitable advances in equipment design and improved techniques of freezing should help solve these problems.

In the description of the ideal apparatus for the application of liquid nitrogen; Elton R., mentioned that it should be simple to operate, safe to use, portable and should enable the operator to freeze to an adequate depth.

In trained hands cryosurgery has already proved to be a valuable tool. No doubt as improvements in equipment and techniques are developed, it will become even more valuable because of its unique properties.

The problems attendant with commercially available probes have been documented and the need for improved devices has been recognized.

See the following references:

REFERENCES

1. Crumy H. M.,
   Physical Modalities of Therapy, Chapter 38, Dermatology 2nd Ed., Moschella S. L., Hurley H. J., W. B. Saunders Co., Philadelphia 1985, pp 1996-2001
2. Elton R. F.
   Cryosurgery for Skin Cancer and Cutaneous Disorders, Zacarian S. A., The C. V. Mosby Co., St. Louis, 1985, PP 313-321
3. Elton, R. F.
   Complications of Cutaneous Cryosurgery J-Am.-Acad. Dermatol. April, 1983 (8) (4) PP 513-9
4. Gage A. A.
   Deep Cryosurgery in Skin Surgery, Epstein E. Charles C. Thomas, Publisher, Springfield, 1982, pp 857-877

It is an object of the present invention to provide an improved method and apparatus for performing cryotherapy while avoiding the problems of the prior art.

It is a further object of the present invention to provide an improved probe which is of a needle-like configuration and adapted for insertion through the skin allowing a gas to be directed through the hollow of the needle and to be discharged from the needle into the atmosphere.

BRIEF DESCRIPTION OF THE FIGURES

FIGS. 6-8 are diagrammatic views employing the use of a hook-shaped needle according to this invention.

FIG. 9 is a diagrammatic view showing the use of the needle in FIGS. 6 and 7 as applied to a gaseous source.

FIG. 13 shows a needle of a different configuration while

FIGS. 16A to 21A depict various needle configurations employing different portions of insulation.

FIGS. 16B to 21B depict the needles in FIGS. 16A to 21A used in therapeutic applications.

DETAILED DESCRIPTION OF FIGURES

Figure 1:
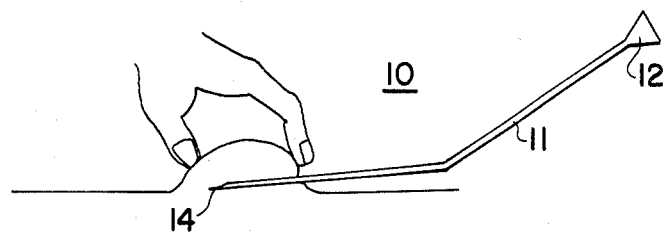
FIG. 1 is diagrammatic view showing a use of a needle according to this invention and employed with a cyrotherapeutic technique.

Referring to FIG. 1, there is shown a needle 10 which is employed in accordance with this invention. Also shown in FIG. 1 is the hand of a physician who is going to utilize the needle 10 in order to perform a cyrotherapeutic operation as the removal of a lesion from the patient.

As seen in FIG. 1 and as will be further evidenced in regard to the description to follow, each needle is composed of a shaft 11 and a headpiece 12. Essentially, the needle is a hollow tubular member having a sharpened point 14 which point 14 terminates in an opening. The headpiece 12 is the connecting part which connects the hollow shaft to the cyro-surgery apparatus. Essentially, the cyro-surgery apparatus is a source of cyrogen which for example may be liquid nitrogen or nitrous oxide. This source contains the pressurized cyrogen which is inserted into the needle via the headpiece 12. The headpiece 12 is of a conventional design and may be implemented in many different ways according to the source of cyrogen to be utilized.

Thus, the headpiece 12 may be a threaded screw member or some other coupling device to enable one to couple the needle and shaft into a source of pressurized gas. The headpiece 12 may be integrally formed with the shaft 11 and thus form a complete integral structure. The shaft 11 of the needle is formed of a strong and sterilizable material such as stainless steel.

It is understood as will be explained that due to the simple construction of the needle 10 it can be used in an operation and then disposed of. The shaft 11 may be of any diameter permitting easy effective cooling by the gas which is applied through the internal hollow of the shaft 11. The usually used diameters of needle 11 are between 0.5 to 1.0 millimeters. It is of course understood that the diameter employed may vary according to the particular procedure employed.

As can be seen from FIG. 1, the needle 10 has a bend forming an angle which angle may be up to 130°. A typical length of the shaft may be greater than 3.5 centimeters while typical lengths employed are between 8 to 16 centimeters to allow the headpiece 12 to be far enough from the surface of the skin to avoid and prevent any danger which may occur from contact with the cold parts of the apparatus or due to leakage.

This length is also selected to enable the practitioner to obtain a proper field of view while performing the method to be described.

Figure 2:
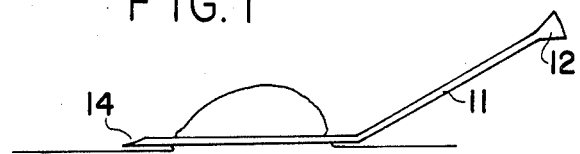
FIG. 2 is a diagrammatic view showing the needle of FIG. 1 being inserted through the skin.

As will be further described in conjunction with various other Figures, the shape of the needle may vary according to the particular techniques employed. As seen from FIG. 1, the physician grasps the skin above the affected proceeds to insert the needle from one point so that the needle passes through the skin as shown in FIG. 2 whereby the tip or point 14 passes directly through the area to be treated.

Figure 3:
FIG. 3 is a diagrammatic view showing the needle of FIG. 1 in position.

As seen in FIG. 3, the angle portion of the needle is then positioned to lie beneath the skin at a predetermined depth based on the formed angle. Thus, as one can immediately see from FIG. 3, the angle portion of the needle is located directly beneath the surface of the skin at a given depth while the point 14 is positioned within the atmosphere.

Figure 4A:
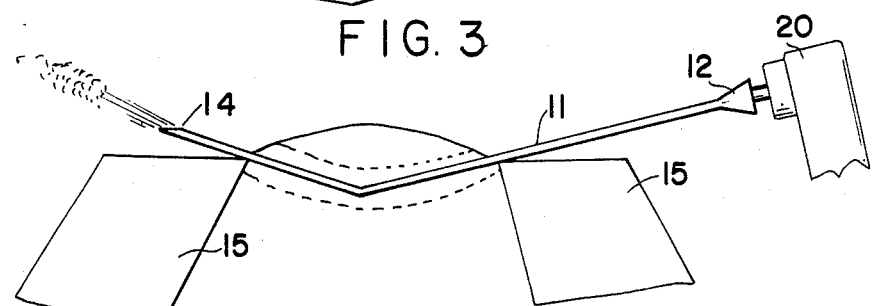
FIG. 4A is a diagrammatic view showing the needle coupled to a source of gas to remove or freeze a lesion according to the techniques and methods of this invention.

As shown in FIG. 4A, a source 20 containing a cyrogen is coupled to the headpiece 12. As one can see from FIG. 4A, the gas is passed through the needle thus lowering the temperature as well as the temperature of the surrounding tissue. The gas as seen in FIG. 4A is discharged via the point opening 14 into the atmosphere. The patient's skin which is under both the visible parts of the needle is protected by suitable sheets 15 of insulating material such as Teflon, nylon, paper towels or any other suitable material. This material 15 is used to protect the patient's skin from contact with the visible cold parts of the needle.

Thus, as seen in FIG. 4A, an ice cylinder designated by the dashed lines will be formed around the imbedded part of the needle in the deeper tissues. The temperature can be lowered by increasing the time of gas passage until a desired temperature is reached. As one can ascertain from the description above, the needle shown in FIG. 1 contains a bend and is angulated with the direction of the opening 14 being in the upward direction. It is of course understood that the bend may be located at any point along the shaft as between the junction of the interior third with the posterior third or at the middle of the needle. The angle as indicated may be more or less than 130°, but 130° is considered desirable.

As will be further explained, there are many configurations which will be employed to accommodate needles including needles which are insulated partially to allow one to effectuate concentrated freezing in desired directions or locations. These needles employing other configurations will be explained. In any event, it should be understood from the above description that the main objective of the present invention is to provide a specifically shaped needle which needle for example contains a shaped area allowing deep penetration into the skin. The needle being of a small diameter and having a sharpened point can then be inserted at any desired depth. By means of a headpiece associated with the hollow shaft, a source of cyrogen can be accommodated and pass through the needle. The needle will allow the gas to be discharged due to the fact that the needle is inserted into the skin and then pushed so that the point end and opening is pushed through the skin. In this manner the physician utilizes the needle in the simple procedure shown in FIGS. 1–4A and eliminates the necessity of performing any surgical procedures as well as eliminating the need for providing the patient with an anesthetic due to the simple procedures involved.

Figure 4B:
FIG. 4B is a diagrammatic view depicting the apparatus of FIG. 4A and showing one technique for determining the depth of freezing.

Referring to FIG. 4B, there is shown the apparatus of FIG. 4A wherein the gas is being passed through the hollow of the needle 11. Essentially, the physician can determine the extension of whitish freezing areas as 21 and 22 around the points of contact between the surface and the appropriate portions of the needle. This whitish area represents another indicator for the determination of the extent of freezing.

Figure 5:
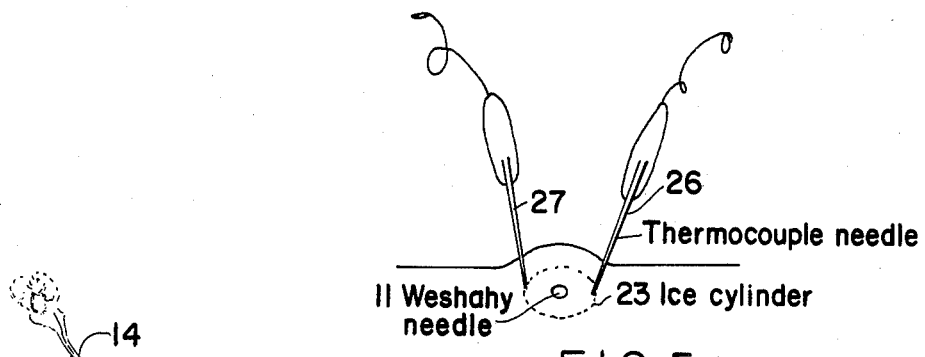
FIG. 5 is diagrammatic view depicting a transverse section of the treated area as in FIG. 4B showing the use of thermocouples to determine temperature.

In regard to FIG. 5 there is shown two thermocouple probes 27 and 26. The thermocouple needles are inserted into the area being treated by the needle 11 and are utilized to measure the temperature of the area to determine proper freezing of the area.

Referring to FIGS. 6-9, there is shown a different needle configuration and a procedure which is accomplished utilizing the needle.

As seen in FIG. 6, the needle 31 is curved or of a hook shape configuration. The needle 31 again has a hollow shaft having an opening 32 to allow gas inserted into the needle by means of a headpiece 12 (not shown) to be discharged into the atmosphere. To the right of FIG. 6, there are shown two views showing the surgeon's hands in raising the skin so that the needle can be inserted as shown in FIG. 7 and then, as indicated in FIG. 8, is pushed so that the opening 32 now extends from the skin.

FIG. 9 shows the same needle 31 accommodating a source of cryogen 36 which is applied to the needle via the headpiece 35. As one can ascertain from FIG. 9, the gas is discharged accordingly. Also shown in FIG. 9 is a clamp 37 which is an insulated clamp and which is held by the physician while directing gas through the needle 31 to enable the physician or an assistant to pull upwardly. The dashed line area shows the area of freezing which would be accommodated utilizing the needle depicted in FIG. 9.

Figure 10:
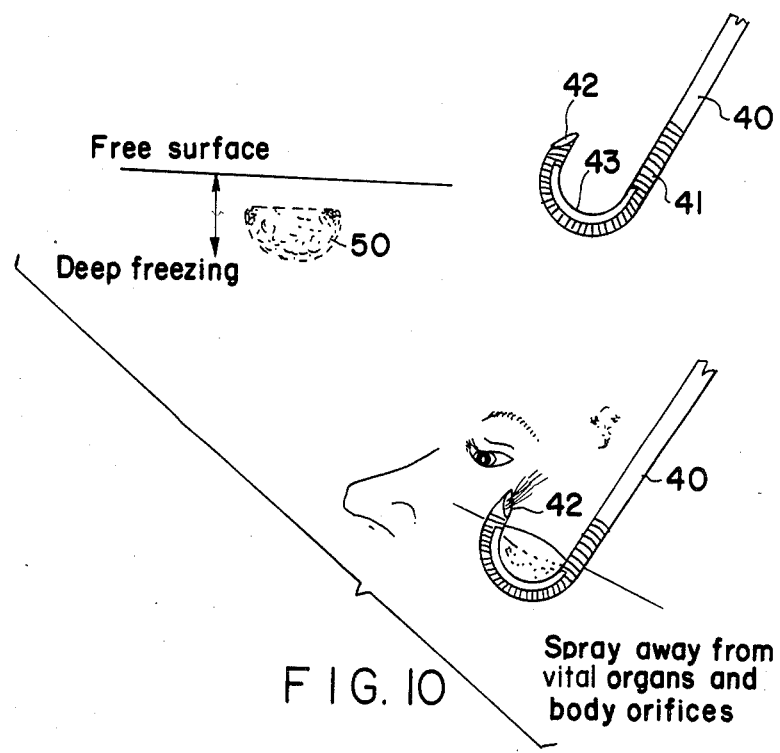
FIG. 10 is a diagrammatic view of a partially insulated needle showing the use of such a needle to remove a particular lesion adjacent a body orifice.

Referring to FIG. 10, there is shown still another example of a hook shaped needle 40. The needle 40 has a layer 41 of insulating material such as a Teflon disposed on a surface. As seen from FIG. 10, the Teflon layer 41 is disposed along the arcuate section of the needle and along the shaft section leaving a portion 43 unexposed. Shown to the left of the needle is a tumor location 50 which essentially is a deep tumor.

As seen from FIG. 10, the needle 40 is then inserted into the skin by means of the above-described techniques and the cryogen gas is applied to the hollow of the needle with the aperture 42 allowing the gas to be expelled and sprayed away from the patient.

Figure 11:
FIG. 11 is a diagrammatic view of one particular needle according to this invention.
Figure 12:
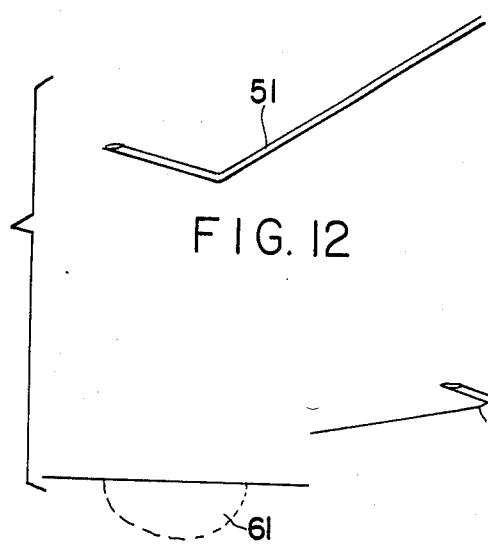
FIG. 12 is a diagrammatic view of another needle employed according to this invention.

FIGS. 11 and 12 depict two different needles 50 and 51 wherein the angle of the bend is less in FIG. 11 than it is in FIG. 12. It is of course understood that both needles can be employed to freeze different types of lesions at different depths. It is also understood that both needles have associated therewith a suitable headpiece for coupling to a source of gas.

Figure 11B:
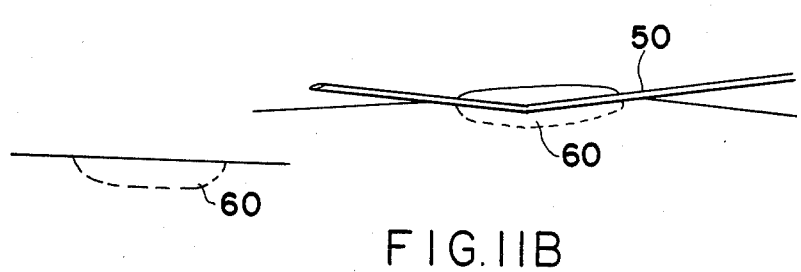
FIG. 11B depicts the needle of FIG. 11 used in a cyrotherapeutic procedure according to this invention.
Figure 12B:
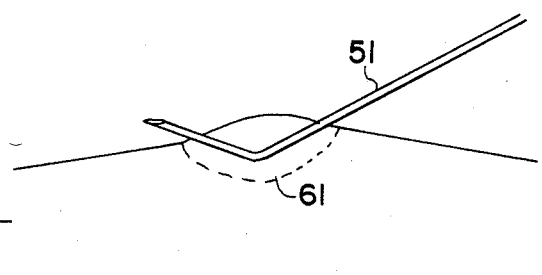
FIG. 12B depicts the needle of FIG. 12 used in a typical application according to this invention.

FIG. 11B shows the use of the needle 50 in regard to a surface lesion 60 while FIG. 12B shows the use of the needle 51 in regard to another surface legion 61.

Figure 13:

FIG. 13 shows another needle configuration 62.

Figure 13B:
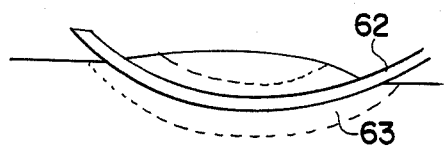
FIG. 13B shows the needles of FIG. 13 utilized in a cyrosurgical procedure.

FIG. 13B shows a needle 62 operating in conjunction with a lesion 63. It is shown that needle 62 is arcuate in configuration having less of a curve then for example the needle shown in FIG. 10.

Figure 14:
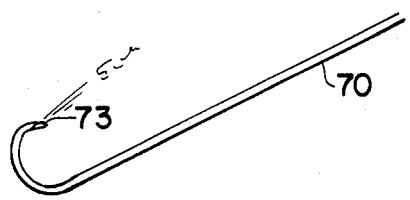
FIGS. 14 and 15 show two different needles of a fish-hook configuration having different gas discharge openings which openings are oriented in different directions.
Figure 15:
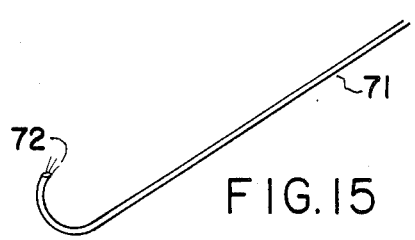

Referring to FIGS. 14 and 15, there is shown two needles 70 and 71 basically each having a straight shaft with the distal end being curved as part of a circle. In any event, as one can ascertain, the opening 72 associated with needle 71 is directed towards the inside of the circle while the opening 73 associated with needle 70 is directed away from the circle. The direction of gas flow is shown in FIGS. 14 and 15.

FIGS. 14 and 15 indicate that the openings in regard to the tip of the needle can be oriented in different planes to therefore direct or discharge the gas in different directions depending upon the particular surgery to be performed.

Figure 14B:
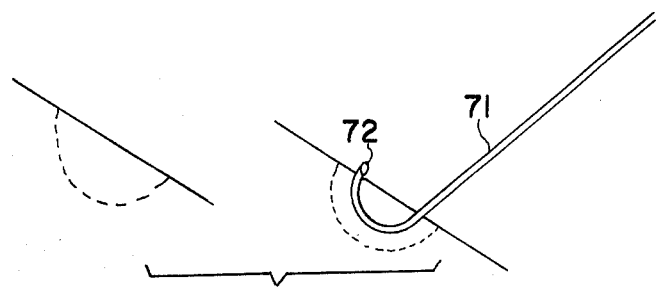
FIGS. 14B and 15B show the needles of FIGS. 14 and 15 respectively used in a cyrotherapeutic operation.
Figure 15B:
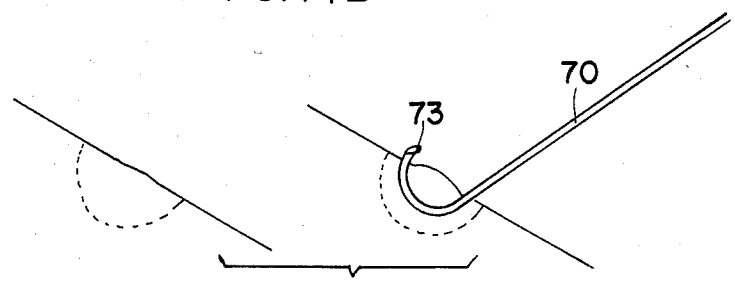
Figure 16A:
Figure 20A:
Figure 21A:
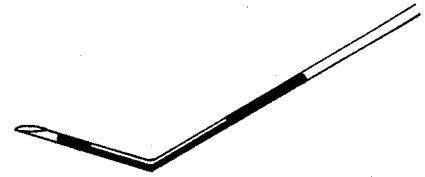
Figure 16B:
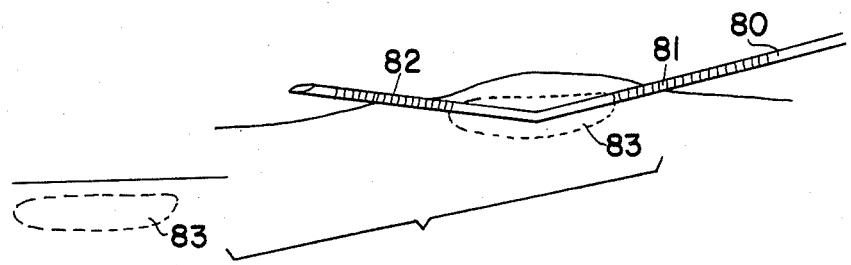

FIGS. 14B and 15B show the use of the two different types of needles depicted in FIGS. 14 and 15 as being utilized to freeze different types of lesions.

FIGS. 16A-21A depict a series of needles having different sections thereof insulated to allow the needle to be utilized to selectively freeze lesions of different sizes and different depths. FIGS. 16B-21B show the needles employed with different lesions. As one can determine, the needle shown in FIG. 16B has a shaft 80 which is insulated in area 81 and 82 leaving the central portion or angular portion exposed. The needle is used to freeze a lesion 83.

Figure 17A:
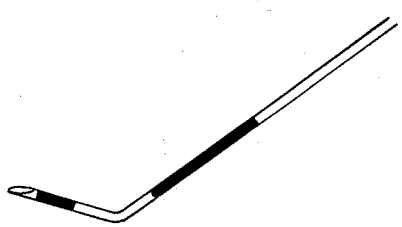
Figure 17B:
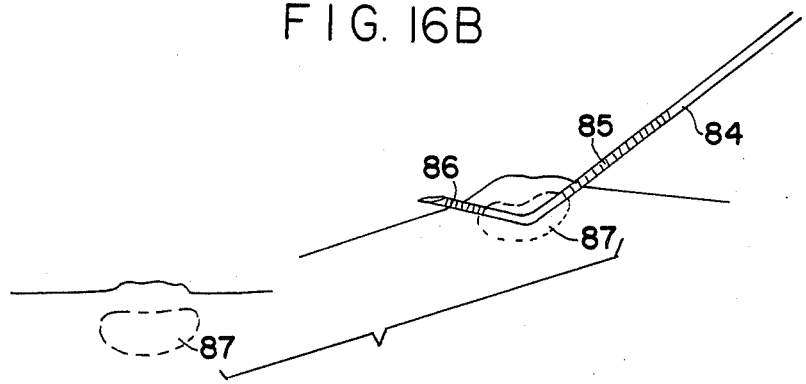
Figure 20B:
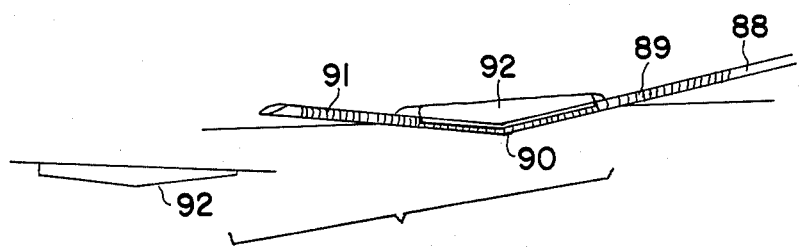

FIG. 17B shows still another needle configuration having a different angular configuration. The needle 84 has areas 85 and 86 which are insulated leaving the angular portion again uninsulated and utilized to remove a lesion 87 shown FIG. 20B shows still another needle 88 having an insulated portion 89, a central insulated portion 90 and an end portion 91. It is noted that the portion 90 associated with the angular bend is insulated at the bottom surface and uninsulated at the top surface and is utilized to freeze a lesion such as 92.

Figure 21B:
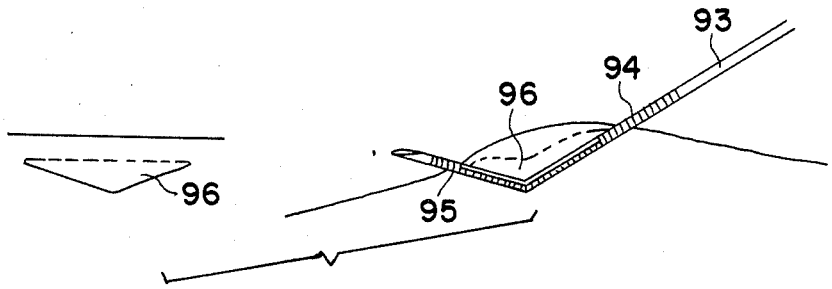

FIG. 21B shows still another needle whereby the angular portion or section is uninsulated at the top surface having insulated section 94 and 95 adjacent to the same and is utilized to remove or freeze a lesion designated by reference numeral 96.

Figure 18A:
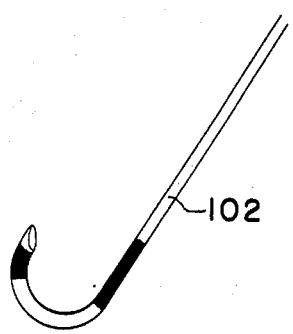
Figure 18B:
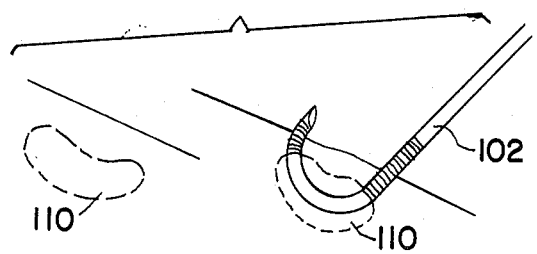
Figure 19A:
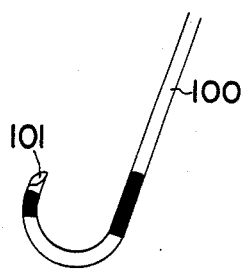

FIGS. 18A, 19A, 18B and 19B show needles which are of hook shaped configurations having different sections thereof insulated with the needle 100 shown in FIG. 19A having a different direction opening from the needle 102 shown in FIG. 18A.

Figure 19B:
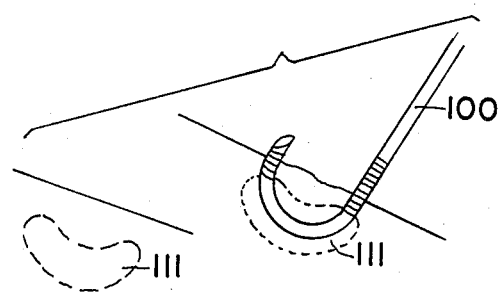

FIGS. 18B and 19B show the needles of 18A and 19A employed to remove tumors as 110 and 111 with saving of the surface tissue.

Referring to FIGS. 23A and 22A, there again is shown bent needles having insulation applied around the outside surfaces thereof near the arcuate bends allowing a portion of the needle to be exposed such as portions 115 and 116. It is noted that the difference between the needles in 23A and 22A involve the directional openings as 117 and 118.

Figure 23A:
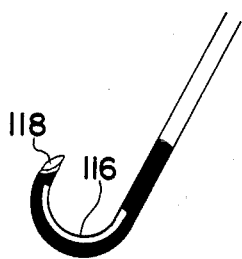
FIGS. 22A and 23A depict alternate embodiments of needles employed with this invention.
Figure 23B:
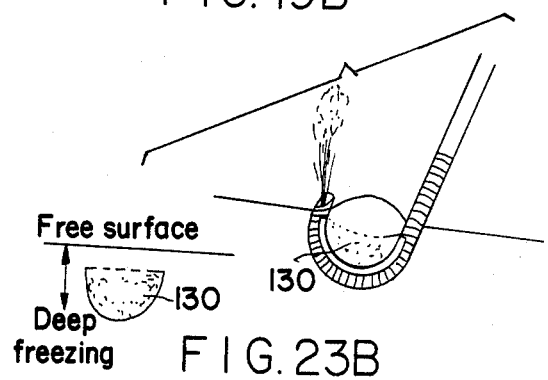
FIGS. 22B and 23B depict needles in FIGS. 22A and 23A utilized in therapeutic applications.
Figure 22A:
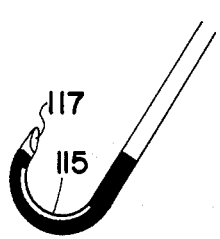
Figure 22B:
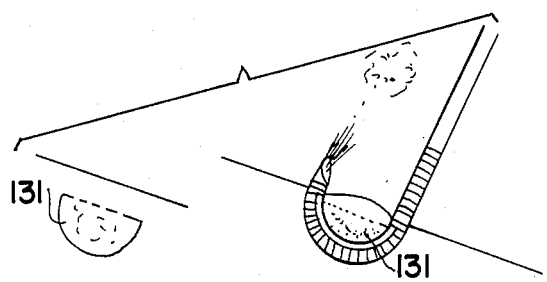

FIGS. 23B and 22B show the needles of FIGS. 22A and 23A being employed to remove tumors 130 and 131 with the direction of gas being discharged through the different orifices in different directions and allowing freezing to occur only in the center.

Figure 24A:
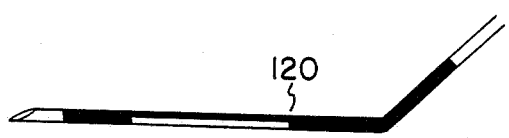
FIGS. 24A and 25A depict alternate embodiments of insulated needles according to this invention.
Figure 25A:
Figure 24B:
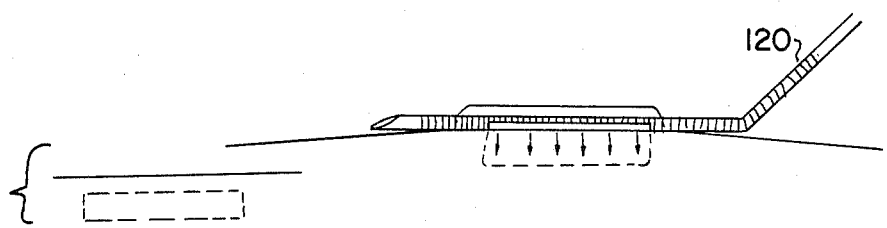
FIGS. 24B and 25B show the needles of FIGS. 24A and 25A utilized in surgical procedures.
Figure 25B:
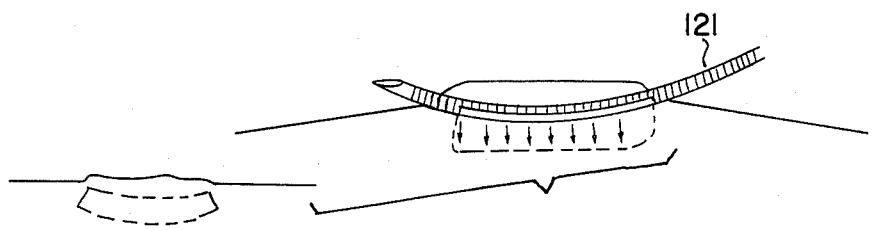

FIGS. 24A and 25A show two different needle configurations 120 and 121 having selective areas covered with insulation to allow the bottom portions of the needle to effectuate freezing in FIGS. 24B and 25B. These are used for obliterations of small blood vessels and other superficial linear lesions.

Figure 27A:
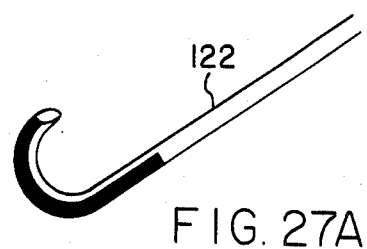
FIGS. 26A and 27A depict alternate embodiments of needles employed according to this invention.
Figure 26A:
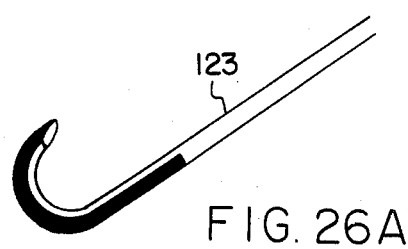
Figure 27B:
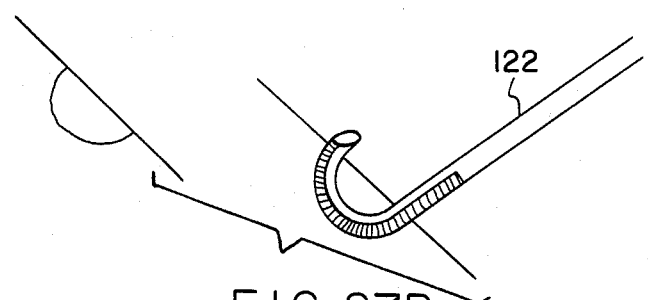
FIGS. 26B and 27B show the needles of FIGS. 26A and 27A utilized in surgical procedures.
Figure 26B:
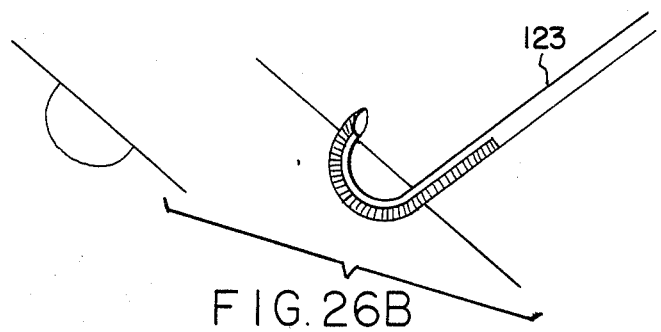

FIGS. 26A and 27A show again different arcuate shaped needles 122 and 123 having the bottom portions thereof insulated to allow the removal of certain types of tumors as indicated in FIGS. 27B and 26B with sparing of deeper tissues.

Figure 28:
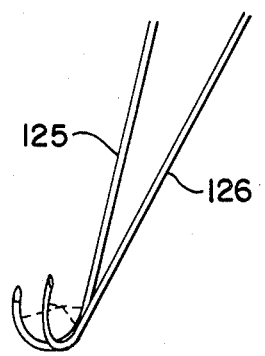
FIG. 28 shows the use of a multiplicity of needles employed during a surgical procedure and according to the methods described in this invention.
Figure 28:
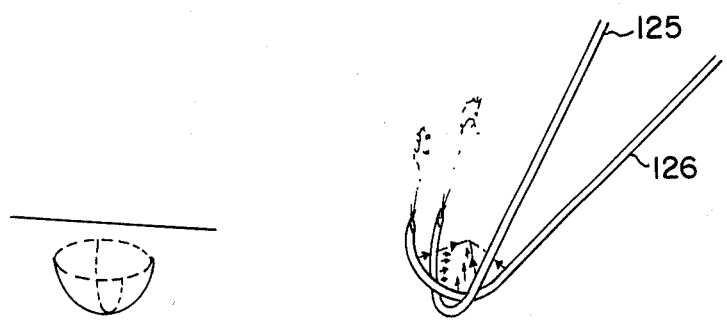

FIG. 28 shows the use of multiple needles 125 and 126 to freeze a given lesion. It is thus obvious that one can utilize multiple needles to effectuate freezing of various different types of tissue at the same time or afterwards.

Thus, from the above it should be apparent to those skilled in the art that various specifically shaped needles may be employed. In any event, all needles are introduced into the skin of a patient by the same technique. All needles accommodate the cryogen or gas by the same type of system. The curve or angle of the needle is a function of the penetration desired and is a function of the depth at which the needle is to be utilized.

Based on such techniques, certain surface portions of the needle can be insulated by the use of suitable insulating materials such as Teflon which permits selective freezing of upper or lower tissues while not affecting surrounding tissues. Thus, for example in regard to the needles depicted in FIGS. 26A and 26B, one can understand that based on the insulation of the outer half surface, freezing occurs only from the inner or upper half surface of the needles. This will allow freezing of the central tissues including the surface so that the extent of freezing will be apparent on the surface. The insulated needles as depicted thus serve multiple purposes and essentially save and avoid damage to surrounding healthy tissues.

As one can ascertain from the above, most of the lesions of the skin which need local excision whether benign, premalignant or malignant can be destroyed easily with minimum local reactions (as edema and haemorrhagic bulla and serous exudation). These usually occur when the cyrosurgery is applied to the surface to reach the deeper tissues. In any event, by the use of the needles as explained and described above, cyrosurgery starts at the required depth directly by insertion of the needles. The above described needles can be imbedded in any part of a lesion to produce upper, middle or lower destruction or can be imbedded around the lesion to destroy the blood supply and surround the lesion by fibrous tissue.

As is also shown in the above-noted Figures, by gentle pulling of the imbedded needle in an upward direction, the skin lesion can be elevated from the underlying structures. This avoids complications as nerve destruction which will occur using other techniques. The above-described techniques can be used in the skin or mucous membranes and also in the body cavities as the oral cavity, vaginal, nose and others as the curved needles direct the exit of gas towards its source and also by the use of a suction machine or isolated cones or tubes the discharged gas can be directed accordingly. The gas in this manner can be extracted safely from the body cavity.

The method and apparatus above described can be used to produce limited destruction of tissues by using a cyrogen with minimal or without surface affection. In this manner one can eliminate unwanted tissues without surgery or without unnecessary openings of the skin. These techniques will therefore prevent the hazards and complications of such surgery and avoid the use of general anesthesia and therefore prevent scar formation or a bleeding field.

The technique can be used in the palliative treatment of inoperable tumors and can be used to reduce the size or relieve compression of malignant tumors and metastasis without the need of wound protection or prolonged wound healing or dressing. As seen for example in FIGS. 24B and 25B, the application of external compression on a straight part of a needle which is passed through a dialated vein the lumen can be sclerossed and obliterated. In this manner as shown in FIG. 28 two or more isolated lower surface needles can be used simultaneously in a cross axis manner to produce destruction in the central focus of an area through simultaneous multisources of freezing. The techniques described above are usually used without anesthesia since the needles produce a pain similar to the pain incurred during an ordinary needle prick.

Furthermore, since the cold gas has an anesthetizing capacity local anesthesia is not resorted to except in unusual cases.

I claim:

1. A method of applying intra-lesional cryotherapy, comprising the steps of:
   inserting a hollow thermally conductive needle having a front opening through the skin of a patient with said needle having a given surface portion adapted to position the same at a given depth according to the location of a lesion to cause said front opening of the needle to protrude from the patient's skin when said given portion is in position and applying a cryogen through the internal hollow of said needle to cause said given portion to freeze tissue in the area of said lesion while said cryogen is being discharged from said front opening of said needle.

2. The method according to claim 1, wherein said given portion of said needle includes a bend at a predetermined angle.

3. The method according to claim 1, further including the step of placing an insulating material about the skin of the patient after inserting said needle to protect the skin during the application of said cryogen.

4. The method according to claim 1, wherein said front opening of said needle is contiguous with a sharp tip for penetrating the skin.

5. The method according to claim 1, wherein the step of inserting includes inserting a needle having a hook-like front portion into the skin of a patient with the hook portion constituting said given portion and having a front which protrudes from the skin for discharging said cryogen.

6. The method according to claim 1, including the further step of selectively insulating portions of said needle prior to insertion of the same to form said given portion of a predetermined configuration.

7. The method according to claim 1, wherein said needle has a diameter between 0.5–1.0 mm and a length greater than 3 cm.

8. The method according to claim 7, wherein the length of said needle is between 8–16 cm.

9. The method according to claim 1, wherein said cyrogen is selected from nitrous oxide and liquid nitrogen.

10. The method according to claim 6, wherein the step of selectively insulating portions of said needle prior to insertion of the same includes insulating said portions with Teflon.

11. The method according to claim 1, further including the step of pulling said needle upwardly while applying said cryogen to raise said skin during application.

12. A method of performing cryosurgery on a lesion associated with the skin of a patient, comprising the steps of:

inserting a relatively long hollow thermally conducting tubular needle through the skin of a patient in the area of said lesion, said needle having a sharpened apex surrounded by a front opening at a first end and having an opening at a second end with said needle having a given shaped portion that is positioned in the area of said lesion when said needle is inserted such that said front opening protrudes from the patient's skin, applying a source of cryogen to said opening at said second end to cause said cryogen to pass through the hollow of said needle and to be discharged through said front opening to freeze tissue in the vicinity of said lesion.

13. The method according to claim 12, wherein the step of inserting includes inserting a hollow stainless steel needle having a bent given shaped portion.

14. The method according to claim 12, wherein the step of inserting includes inserting a hollow stainless steel needle having an arcuate given shaped portion.

15. The method according to claim 12, further including the step of selectively insulating portions of said needle prior to insertion to provide a selected surface area for conduction to selectively freeze said tissue.

16. The method according to claim 12, further including the step of placing an insulating material about the skin of said patient after inserting said needle to protect the skin while applying said cryogen.

17. The method according to claim 12, further including the step of pulling said needle during the application of said cryogen to raise the skin of the patient in said area of said lesion.

18. The method according to claim 12, wherein said front opening is canted to discharge said cryogen in a given direction.

19. A probe to be employed in a cryosurgical operation comprising:

a hollow thermal conducting tubular needle having a front opening at a first end and back opening at a second end, said tubular needle having a given surface portion between said ends of a shape to allow said needle to be inserted into the skin of a patient at a given depth according to the location of a lesion to be removed by freezing the tissue in the area of said lesion with said given surface portion always allowing said front opening at said first end to protrude from the skin of a patient when said needle is inserted to allow cryogen to escape into the atmosphere, means coupled to said second end and adapted to receive a source of a cryogen, including an insulator material surrounding surface portions of said needle which insulated surface portions define a given thermal conducting non-insulated region for selectively freezing said lesion.

20. The probe according to claim 19, wherein said given surface portion is manifested by an angular bend in said tubular needle between said first and second ends.

21. The probe according to claim 19, wherein said surface portion is manifested by an arcuate curve in said tubular needle between said first and second ends.

* * * * *